(12) United States Patent
Yamashita

(10) Patent No.: US 7,037,728 B2
(45) Date of Patent: May 2, 2006

(54) FINE PARTICLE FILM AND PRODUCING METHOD OF THE SAME

(75) Inventor: Ichiro Yamashita, Nara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 56 days.

(21) Appl. No.: 10/617,955

(22) Filed: Jul. 14, 2003

(65) Prior Publication Data

US 2004/0142164 A1 Jul. 22, 2004

Related U.S. Application Data

(63) Continuation of application No. PCT/JP02/11594, filed on Nov. 7, 2002.

(30) Foreign Application Priority Data

Nov. 8, 2001 (JP) .............................. 2001-343526

(51) Int. Cl.
*G01N 33/543* (2006.01)

(52) U.S. Cl. ...................... 436/518; 436/524; 436/532; 435/7.1; 427/299; 427/322; 427/323

(58) Field of Classification Search ................. 435/4, 435/40.5, 40.51; 427/457, 458, 469, 472, 427/561, 299, 322, 323; 422/50; 118/620, 118/621; 436/518, 524, 528, 533, 532
See application file for complete search history.

(56) References Cited

U.S. PATENT DOCUMENTS

| | | | | |
|---|---|---|---|---|
| 5,505,996 A | * | 4/1996 | Nagayama | 427/123 |
| 5,510,481 A | * | 4/1996 | Bednarski et al. | 536/120 |
| 5,670,624 A | * | 9/1997 | Yoshimura et al. | 530/350 |
| 6,107,084 A | | 8/2000 | Onda et al. | |
| 6,124,103 A | * | 9/2000 | Bose | 435/7.1 |
| 6,326,149 B1 | * | 12/2001 | Loewy et al. | 435/6 |
| 6,444,318 B1 | * | 9/2002 | Guire et al. | 428/412 |
| 2001/0031309 A1 | * | 10/2001 | Lee et al. | 427/2.1 |

FOREIGN PATENT DOCUMENTS

| | | |
|---|---|---|
| EP | 0 583 894 | 2/1994 |
| EP | 0583 894 | 2/1994 |
| JP | 4-186158 | 7/1992 |
| JP | 6-256753 | 9/1994 |
| JP | 08-155379 | 6/1996 |
| JP | 8-157497 | 6/1996 |
| JP | 08-245815 | 9/1996 |
| JP | 9-92617 | 4/1997 |
| JP | 11-204774 | 7/1999 |
| WO | WO 85/04111 | 9/1985 |
| WO | WO 93/09143 | 5/1993 |

OTHER PUBLICATIONS

Heusterspreute et al. Amino Acid Sequence of Hores Spleen Apoferritin, 1981, FEBS Letters, vol. 129, No. 2, pp. 322-327.*

"Fabrication and Control of Two-Dimensional Crystalline Arrays of Protein Molecules", K. Nagayama et al., Japanese Journal of Applied Physics, vol. 34, No. 7B, pp. 3947 to 3954.

"Two-Dimensional Molecular Packing of Proteins", Thin Solid Films, vol. 216, No. 1, pp. 99 to 104, Aug. 28, 1992 Sasabe et al.

Yoshimura, H. et al. "Two-Dimensional Protein Array Growth in Thin Layers of Protein Solution on Aqueous Subphases" Langmuir, vol. 10, 1994, pp. 3290-3295, XP002283389.

Takeda, Shigeki et al. "Control of Crystal Forms of Apoferritin by Site-Directed Mutagenesis" Proteins: Structure, Function, and Genetics, vol. 23, No. 4, 1995, pp. 548-556, XP002282919.

* cited by examiner

*Primary Examiner*—Long V. Le
*Assistant Examiner*—Melanie J. Yu
(74) *Attorney, Agent, or Firm*—McDermott Will & Emery LLP

(57) ABSTRACT

To provide fine particle films including fine particles which are arranged at a high density in a highly accurate and regular manner is enabled. The fine particle film is a fine particle film including a substrate and plural number of protein fine particles which are arranged on the surface of the substrate in a plane direction parallel to the surface of the substrate, wherein each of the protein fine particles has plural number of first binding sites and one or more second binding sites respectively including a condensed amino acid, and each of the first binding sites binds to other first binding site carried by an adjacent fine particle while the second binding site binds to the substrate, wherein at least a part of the condensed amino acids constituting the second binding site are substituted.

5 Claims, 10 Drawing Sheets

(a)

(b)

(c)

(a)

(b)

(a)

(b)

(a)

(b)

(c)

(d)

FINE PARTICLE FILM AND PRODUCING METHOD OF THE SAME

This application is a continuation of PCT/JP02/11594 filed Nov. 7, 2002.

FIELD OF THE INVENTION

The present invention relates to processes for producing a fine particle film, and particularly, relates to techniques to arrange fine particles having the size of around several ten nanometers in a highly accurate and regular manner.

BACK GROUND OF THE INVENTION

Fine particles have a great ratio of the surface area to the volume thereof, and they generally behave in a different manner from materials having small ratio of the surface area to the volume. For example, fine particles of inorganic materials such as titanium oxide, zinc oxide and the like have eliminating action of ultraviolet ray, antibacterial action, catalytic action and the like.

Among fine particles of inorganic materials, fine particles having a diameter in a nanometer size (superfine particles) are expected to exhibit a quantum effect. Accordingly, industrial utilization of the fine particles has drawn attention. In particular, in respect of superfine particles having the diameter in nanometer size, there is an urgent need to develop industrial manufacturing techniques of elements utilizing the quantum effects.

Protein fine particles having the diameter of about 10 to 20 nm have drawn attention in regard to utilization for biosensors and the like. Particularly, among various protein fine particles, there exist fine particles capable of including inorganic materials inside. Such protein fine particles have both features of fine particles of the inorganic materials as described above and of fine particles of a protein.

The fine particles described hereinabove usually have distributed in the form of a colloidal solution. However, it is disadvantageous in efficient utilization of the fine particle functions in the colloidal solution as it is. Therefore, techniques which allow industrially efficient utilization of the functions of fine particles have been sought in which the aforementioned colloidal solution is utilized as a raw material.

Conventionally, two-dimensional crystal films comprising protein fine particles have been utilized in crystal structure analyses of a protein by an electron microscope. In this analysis, a two-dimensional crystal film comprising the protein fine particles is produced by filling a colloidal solution of the protein fine particles in a trough, and concentrating the protein fine particles on a gas-liquid interface of this colloidal solution. According to this process, because the two-dimensional crystal film is formed on the gas-liquid interface, the two-dimensional crystal film is liable to be disrupted through vibration.

Thus, as a technique which can be industrially utilized in an efficient manner, methods to arrange fine particles on a substrate have been believed to be most efficient. Therefore, to establish techniques for readily forming an ideal fine particle film on a substrate with fine particles being regularly arranged at a high density has been desired.

As a technique for arranging protein fine particles on a substrate developed heretofore, a transfer method developed by Yoshimura et al. (*Adv. Biophys.*, Vol. 34, p99–107 (1997)) is explained below with reference to FIG. 12.

First, in the step shown in FIG. 12(*a*), a liquid 24 with protein fine particles 45 dispersed therein is injected into a sucrose solution 23 having the concentration of 2% using a syringe 25.

Next, in the step shown in FIG. 12(*b*), the liquid 24 is elevated up to the surface of the sucrose solution 23.

Next, in the step shown in FIG. 12(*c*), the liquid 24 reached to the gas-liquid interface first forms an amorphous film 26 of the protein fine particles, and the protein fine particles 45 reached afterwards come to attach beneath the amorphous film 26.

Next, in the step shown in FIG. 12(*d*), a two-dimensional crystal film 27 of the fine protein fine particles 45 is formed beneath the amorphous film 26. Then, as is illustrated in FIG. 12(*d*), on a film 28 including the amorphous film 26 and the two-dimensional crystal film 27 of the protein fine particles 45, disposed a substrate 21 (silicon wafer, carbon grid, glass substrate or the like), thereby transferring the film 28 to the surface of the substrate 21.

However, according to the aforementioned conventional method, it is highly possible that a breakage of the film 28 occurs in the step shown in FIG. 12(*d*), and it is also highly possible that a part of the protein fine particles of the two-dimensional crystal film 27 may fall away upon the transfer. Accordingly, there are problems involving difficulties in transferring a two-dimensional crystal film having a great area to a substrate without failure.

Therefore, according to the aforementioned method of Yoshimura et al., there is disclosed a method to accelerate the transfer of protein fine particles onto a substrate surface by treating the substrate surface with aminopropylmethoxy silane so that the substrate surface is positively charged at pH of around 7, in instances where the protein has negative charge at pH of around 7. In addition, it has been also revealed that protein fine particles are liable to bind with each other.

However, when the state of transfer of the protein fine particles to the substrate in the two-dimensional crystal film which was obtained according to the method described above is observed, with SEM or AFM, directions of symmetric axes of the protein fine particles are revealed to be random. Such random directionality results from the sites being random where the protein fine particles contact with the substrate in the method described above. Therefore, according to the method described above, protein fine particles may form a comparatively aggregated structure, however, it is difficult to obtain a two-dimensional crystal film having protein fine particles arranged at a high density in a highly accurate and regular manner, with directions of the symmetric axes of the protein fine particles being coordinated. In other words, directional control of the crystal axis of the two-dimensional crystal film is extremely difficult.

DISCLOSURE OF THE INVENTION

The present invention was achieved to solve the problems described above, and an object of the present invention is to provide a fine particle film with fine particles having a diameter in a nanometer size which are arranged at a high density in a highly accurate and regular manner.

To achieve the above-described object, the present invention concerns a fine particle film comprising a substrate and plural number of protein fine particles which are arranged on the surface of the substrate in a plane direction parallel to the surface of the substrate, wherein each of the protein fine particles has plural number of first binding sites and one or more second binding sites respectively comprising a condensed amino acid, and each of the first binding sites binds to other first binding site carried by an adjacent fine particle while the second binding site binds to the substrate, wherein at least a part of the condensed amino acids constituting the second binding site are substituted.

In addition, the present invention concerns a process for producing a fine particle film comprising a substrate and plural number of protein fine particles which are arranged on the surface of the substrate in a plane direction parallel to the surface of the substrate, wherein each of the protein fine particles has plural number of first binding sites comprising a condensed amino acid, and each of the first binding sites binds to other first binding site carried by an adjacent fine particle, said process comprising: generating a second binding site in each of the protein fine particles by substituting a part of the condensed amino acids constituting each of the protein fine particles with a basic amino acid; and making the substrate bind to the second binding site by bringing the protein fine particles into contact with a negatively charged substrate.

Moreover, the present invention concerns a process for producing a fine particle film comprising a substrate and plural number of protein fine particles which are arranged on the surface of the substrate in a plane direction parallel to the surface of the substrate, wherein each of the protein fine particles has plural number of first binding sites comprising a condensed amino acid, and each of the first binding sites binds to other first binding site carried by an adjacent fine particle, said process comprising: generating a second binding site in each of the protein fine particles by substituting a part of the condensed amino acids constituting each of the protein fine particles with an acidic amino acid; and making the substrate bind to the second binding site by bringing the protein fine particles into contact with a positively charged substrate.

Further, the present invention concerns a process for producing a fine particle film comprising a substrate and plural number of protein fine particles which are arranged in a plane direction parallel to the surface of the substrate on the surface of the substrate, wherein each of the protein fine particles has plural number of symmetric axes; each of the protein fine particles has plural number of first binding sites comprising a condensed amino acid; and each of the first binding sites binds to other first binding site carried by an adjacent fine particle, said process comprising: selecting a specified single symmetric axis among the plural number of symmetric axes by generating a second binding site in each of the protein fine particles through substituting a part of the condensed amino acids constituting each of the protein fine particles with a basic amino acid; and making the substrate bind to the second binding site by bringing the protein fine particles into contact with a negatively charged substrate.

Furthermore, the present invention concerns a process for producing a fine particle film comprising a substrate and plural number of protein fine particles which are arranged in a plane direction parallel to the surface of the substrate on the surface of the substrate, wherein each of the protein fine particles has plural number of symmetric axes; each of the protein fine particles has plural number of first binding sites comprising a condensed amino acid; and each of the first binding sites binds to other first binding site carried by an adjacent fine particle, said process comprising: selecting a specified single symmetric axis among the plural number of symmetric axes by generating a second binding site in each of the protein fine particles through substituting a part of the condensed amino acids constituting each of the protein fine particles with an acidic amino acid; and making the substrate bind to the second binding site by bringing the protein fine particles into contact with a positively charged substrate.

BEST EMBODIMENT FOR CARRYING OUT THE INVENTION

Figure 1:
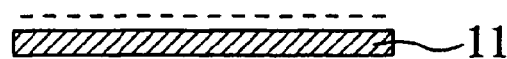
FIG. 1 is a drawing schematically illustrating the process for producing a two-dimensional crystal film according to embodiment 1. In the FIG. 1, (a) illustrates a step for treating the substrate 11 to give negative charge; (b) illustrates a step to immerse the substrate 11 into a liquid 16 with apoferritin fine particles 15 dispersed therein; and (c) illustrates a step to remove the substrate 11 from the liquid 16.
Figure 1:
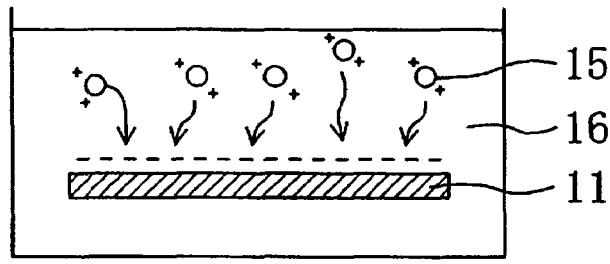
Figure 1:
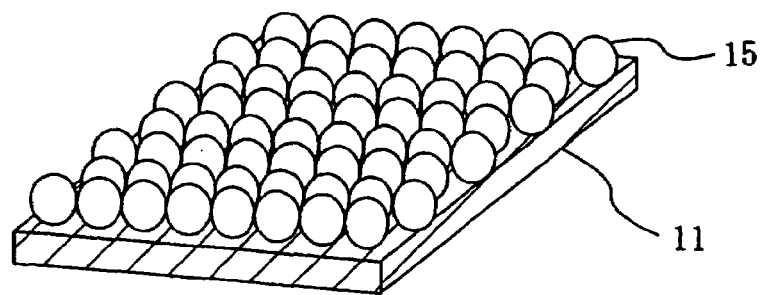

The present invention is explained below in detail.

According to the two-dimensional film obtained by conventional methods described hereinabove, the protein fine particles are arranged in a state whose symmetric axes have random directions. Accordingly, periodic structure is not found. It is believed that this is due to the absence of specificity of the interaction among the protein fine particles within the two-dimensional crystals. Therefore, the protein fine particles aggregate to minimize the surface energy thereof, leading to the random direction of the symmetric axes of the protein fine particles.

Accordingly, the present inventor envisaged that a two-dimensional crystal film having a periodic structure can be produced utilizing a symmetric property of protein fine particles by arranging the protein fine particles in a state whose symmetric axes have a specified direction for the substrate. In other words, it was believed that a two-dimensional crystal film can be obtained having protein fine particles arranged at a high density in a highly accurate and regular manner through specific interactions of the protein fine particles by bringing all of the protein fine particles to a single direction and suppressing free rotation of the protein fine particles, when the protein fine particles are arranged on a substrate.

Embodiments of the present invention explained below are provided on the basis of the above speculation. Embodiments of the present invention are explained with reference to the accompanying drawings. For a convenience, constitutive elements which are common in each of the embodiments are denoted by the identical reference numeral. Further, the term "bind" referred to herein means "fix via an attraction with each other", unless otherwise specified.

Embodiment 1

In this embodiment, a process for producing a two-dimensional crystal film having fine particles arranged at a high density in a highly accurate and regular manner on the surface of a substrate is explained.

Summary of the process for producing the two-dimensional crystal film according to this embodiment is first explained below with reference to FIG. 1.

First, in the step illustrated in FIG. 1(a), a substrate 11 is provided, and the surface thereof is treated to have negative charge.

Next, in the step illustrated in FIG. 1(b), a liquid 16 is provided having apoferritin fine particles 15 dispersed therein of which part being positively charged. The substrate 11 is immersed in the liquid 16. Accordingly, positive charge and negative charge are attracted with each other, and thus apoferritin fine particles 15 are bound on the surface of the substrate 11 which had been treated to have negative charge.

Next, in the step illustrated in FIG. 1(c), the substrate 11 is removed from the liquid 16.

A two-dimensional crystal film of the apoferritin fine particles 15 formed on the surface of the substrate 11 is obtained via the steps described hereinabove.

Next, each of the steps is explained in more detail.

According to this embodiment, the process of Yokokawa et al. (Heisei 11 nendo, Shin-Energy, Sangyo Gijyutsu Sogo Kaihatsu Kikou Shinki Sangyo Sozo-gata Teian Koubo Jigyou Kenkyuu Seika Houkoku-syo "Shinki na Display heno Ouyou wo mezashita Chameleon-gata Hassyoku Shisutemu no Sousei", March, Heisei 12) is employed to form a SAM (self assembly monolayer) film of carboxyethyltrimethoxysilane on the substrate 11 in order to make the surface of the substrate 11 negatively charge in the step illustrated in FIG. 1(a).

According to this embodiment, in the step illustrated in FIG. 1(b), the substrate 11 obtained in the step illustrated in the above FIG. 1(a) is immersed in the liquid 16 having apoferritin fine particles 15 dispersed therein. The apoferritin fine particles 15 used in this embodiment are those obtained from ferritin which had been extracted from a bovine organ such as spleen, liver or the like. The apoferritin fine particle 15 is a protein fine particle having an extremely high symmetric structure, which includes a four times symmetric axis S4, a three times symmetric axis S3 and a twice symmetric axis S2. For easy understandings, the apoferritin fine particle 15 is herein explained regarding as a substantially cubic body.

Figure 2:
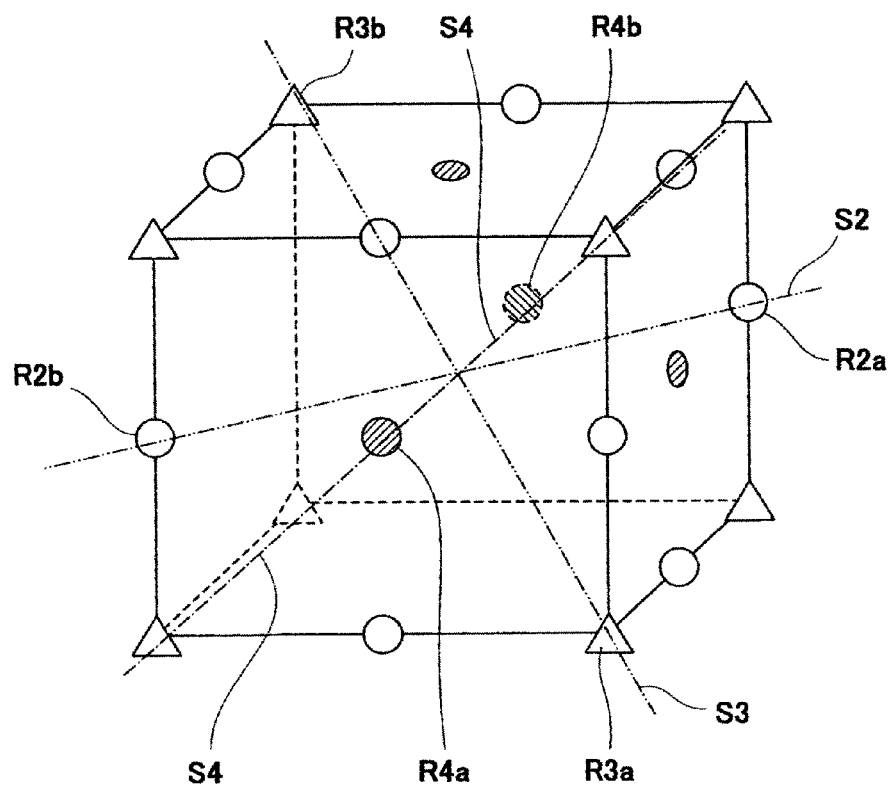
FIG. 2 is a drawing schematically illustrating the apoferritin fine particles 15 used in this embodiment.

FIG. 2 is a drawing schematically illustrating the apoferritin fine particle 15 used in this embodiment. When viewed the apoferritin 15 as a cubic, the four times symmetric axis S4 passes through each center of the 6 faces of the cubic; the three times symmetric axis S3 passes through each apex of the cubic; and the twice symmetric axis S2 passes through the mid point of each edge of the cubic. The symmetric axes are now explained in more detail. The four times symmetric axis S4 is an axis passing through the sites R4a and R4b. The three times symmetric axis S3 is an axis passing through the sites R3a and R3b. The twice symmetric axis S2 is an axis passing through the sites R2a and R2b. For a reference, in this Figure, the four times symmetric axis S4, the three times symmetric axis S3 and the twice symmetric axis S2 are representatively illustrated for each one axis.

The apoferritin fine particle 15 can form two pairs of salt bridges via a divalent cation with another apoferritin fine particle 15 at each site R2 in the vicinity of the twice symmetric axis S2. Moreover, the apoferritin fine particle 15 used in this embodiment is subjected to genetically engineered modification so that each site R3 in the vicinity of the three times symmetric axis S3 has positive charge. The aforementioned salt bridge and genetically engineered modification in the apoferritin fine particle 15 in this embodiment is explained below in detail.

Figure 3:
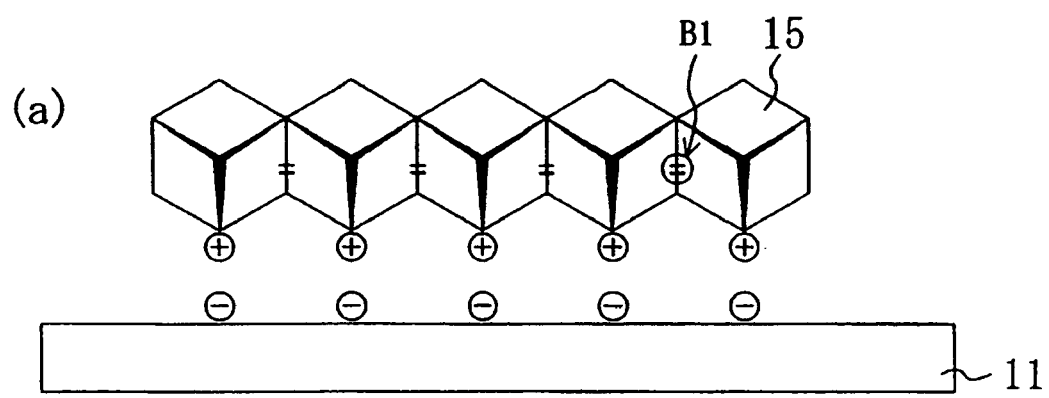
FIG. 3 is a drawing for explaining the step shown in FIG. 1(b) in more detail: (a) is a cross-sectional drawing; and (b) is a top view of the same.
Figure 3:
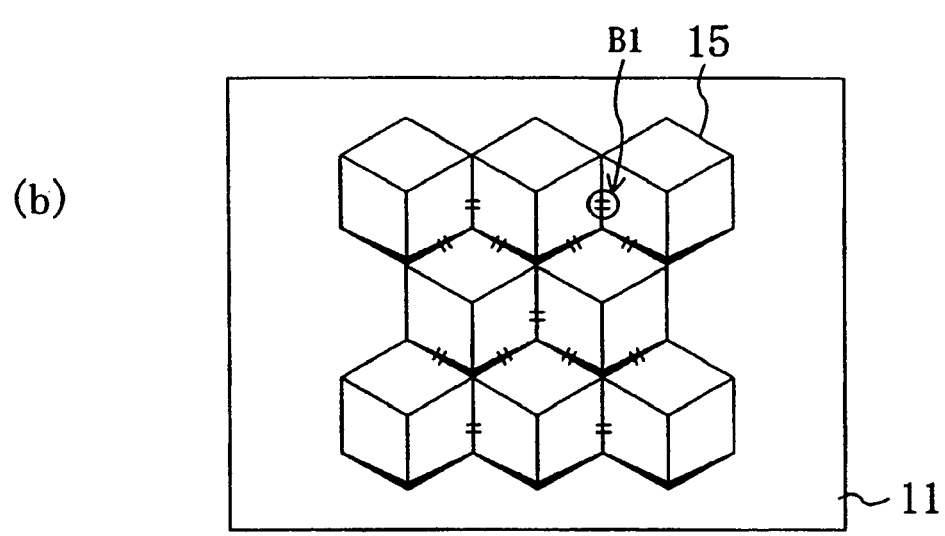

FIG. 3(a) and FIG. 3(b) are a cross-sectional drawing; and a top view illustrating the step shown in FIG. 1(b) in more detail. The apoferritin fine particles 15 bind to the surface of the substrate 11 at either one of the sites R3 in the vicinity of the three times symmetric axis S3 by means of the electrostatic interaction through using the liquid 16 prepared as described above and the substrate 11. Upon the binding, the apoferritin fine particles 15 are sparsely present on the surface of the substrate 11 in a state where the three times symmetric axis S3 directs almost perpendicular to the surface of the substrate 11. In addition, when the binding of the apoferritin fine particles 15 to the surface of the substrate 11 proceeds, adjacent apoferritin fine particles 15 form salt bridges B1 with each other at the sites R2, as shown in FIG. 3(a). Therefore, the particles bind to the surface of the substrate 11 while forming salt bridges B1 with each other at the sites R2 in a state where the three times symmetric axis S3 directs almost perpendicular to the surface of the substrate 11. That is, as shown in FIG. 3(b), all apoferritin fine particles 15 are arranged in a closest manner on the surface of the substrate 11.

The event described above occurs successively on the surface of the substrate 11, and thus results in the formation of a two-dimensional crystal film which is apparently six times symmetry viewed from the top, but is actually three times symmetry, as shown in FIG. 3(b). The apoferritin fine particles 15 are negatively charged in their entirety at this time, therefore, the apoferritin fine particles 15 are not bound so as to overlay the first layer of the apoferritin fine particles 15 which had been deposited. Consequently, a single layered film of apoferritin is thereby formed.

Figure 4:
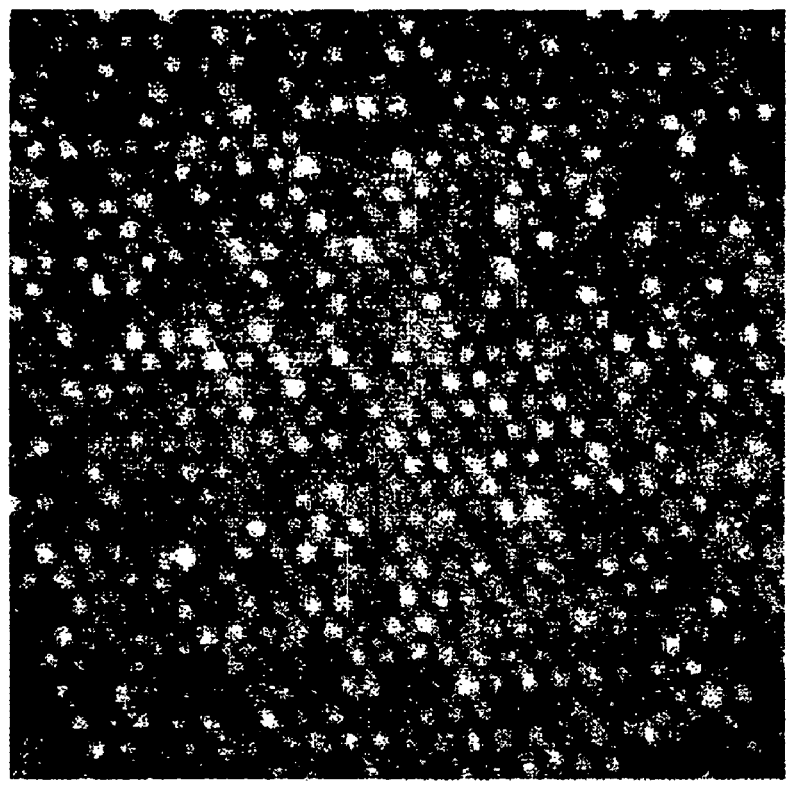
FIG. 4 is an electron microscopic photograph of the two-dimensional crystal film obtained according to the embodiment 1.

FIG. 4 is an electron microscopic photograph of the two-dimensional crystal film obtained according to this embodiment. The two-dimensional film schematically illustrated in FIG. 3(b) is a film with no clearance at all. However, because actual apoferritin fine particles 15 are almost spherical, clearance exists in the film as shown in FIG. 4.

According to this embodiment, as shown in FIG. 4, a two-dimensional crystal film is obtained having apoferritin fine particles 15 arranged at a high density in a highly accurate and regular manner.

In particular, according to this embodiment, a two-dimensional crystal film is easily obtained having apoferritin fine particles 15 arranged at a high density in a highly accurate and regular manner by immersing the substrate 11 into the liquid 16. In other words, in the process according to this embodiment, any operation required for high accuracy is not included at all when the substrate 11 is brought into contact with the liquid 16. Therefore, it is well suited to mass production.

Although the substrate 11 was immersed into the liquid 16 in the step illustrated in FIG. 1(b) according to this embodiment, as is shown in the aforementioned method of Yoshimura et al., it is also possible to use a process in which a two-dimensional crystal film is transferred on the surface of the substrate 11. In brief, any process may be used as long as contact between the liquid 16 and the surface of the substrate 11 is allowed.

Additionally, although apoferritin fine particles 15 having extremely high symmetry are used in this embodiment, high symmetry is not necessarily required for the fine particles. By using fine particles having one or more substrate-binding sites that bind to the surface of the substrate 11 (second binding site) and plural number of mutual binding sites which are capable of binding with each other (first binding site), a two-dimensional crystal film having the fine particles arranged at a high density in a highly accurate and regular manner can be obtained. This is caused by the formation of a repeated structure resulting from a regular arrangement on the surface of the substrate 11 for the purpose of minimizing the surface energy, as long as there exist specific interactions of protein fine particles with each other within the two-dimensional crystal film, even in the instances of fine particles with almost no symmetry. Therefore, apoferritin fine particles 15 are used in this embodiment, but not limited thereto in the present invention.

It is more preferred that fine particles having high symmetry are used such as the apoferritin fine particles 15 used in this embodiment, of course. The reason for this preference is that a two-dimensional crystal film with highly accurate and regular arrangement at a high density can be more readily obtained, and that the resulting two-dimensional crystal film also has extremely high symmetry. Examples of the fine particles having extremely high symmetry which may be used instead of the apoferritin fine particles 15 include an approximately spherical protein such as Dps protein, CCMV protein and the like, for example. These proteins can be completely similarly used in this embodiment instead of the apoferritin fine particles 15 by the genetically engineered modification so that they have one or more substrate-binding sites which bind to the surface of the substrate 11 as well as three or more mutual binding sites which are capable of binding with each other.

The mutual binding site of the fine particle may be any site which allows for the binding with each other by at least either one of the interactions among hydrophilic interactions, hydrophobic interactions and complementarities of the dimensional standard, but not limited to the electrostatic interaction of the salt bridge or the like.

The apoferritin fine particle 15 used in this embodiment is explained hereinafter in detail.

The apoferritin fine particle 15 used in this embodiment is a 24-mer of a subunit having the molecular weight of approximately 20,000, and are spherical protein fine particles having the external diameter of the 24-mer as a whole of 12 nm. In general, apoferritin is present in the living body as ferritin. Ferritin is a complex of an apoferritin fine particle with approximately 3,000 molecules of iron oxide ($Fe_2O_3$) which are included in the apoferritin fine particle. The apoferritin fine particle has characteristics to include any of several inorganic material particles such as metal particles, metal oxides or the like. For example, the apoferritin fine particle can include a particle therein such as gold, iron oxide, cobalt oxide or the like. Accordingly, as the apoferritin fine particle 15 for producing the two-dimensional crystal film as described above, those including an inorganic material particle.

Figure 5:
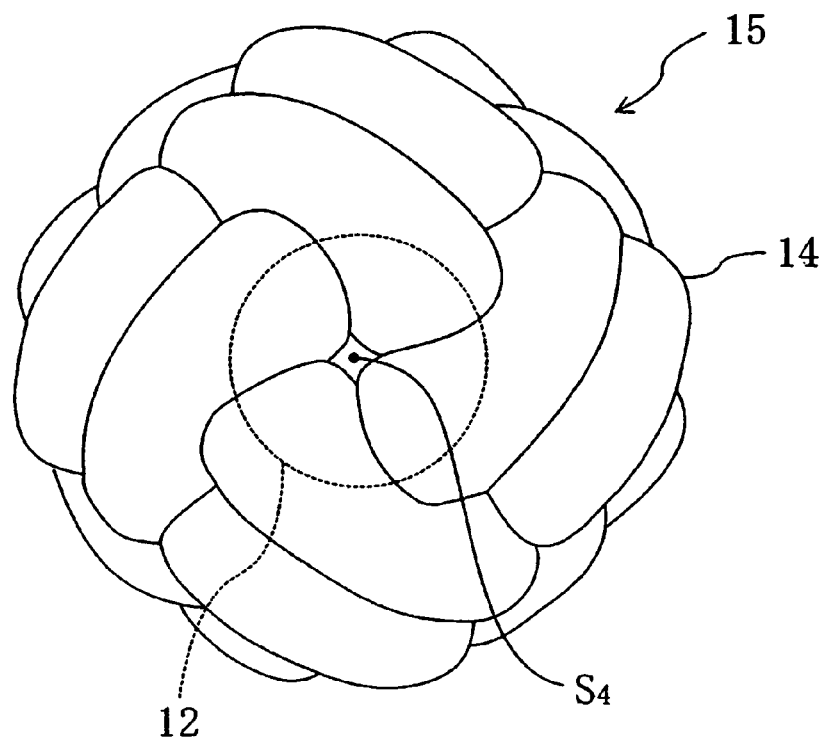
FIG. 5 is a drawing illustrating the structure of the apoferritin fine particles used in the embodiment 1.

FIG. 5 is a drawing illustrating the structure of the apoferritin fine particle used in this embodiment. The apoferritin fine particle 15 used in this embodiment has, as shown in FIG. 5, a structure including: a hollow core 12 with a diameter being approximately 6 nm which is capable of carrying an inorganic material particle; and apoferritin protein molecules (subunits) 14 surrounding the hollow core 12.

Figure 6:
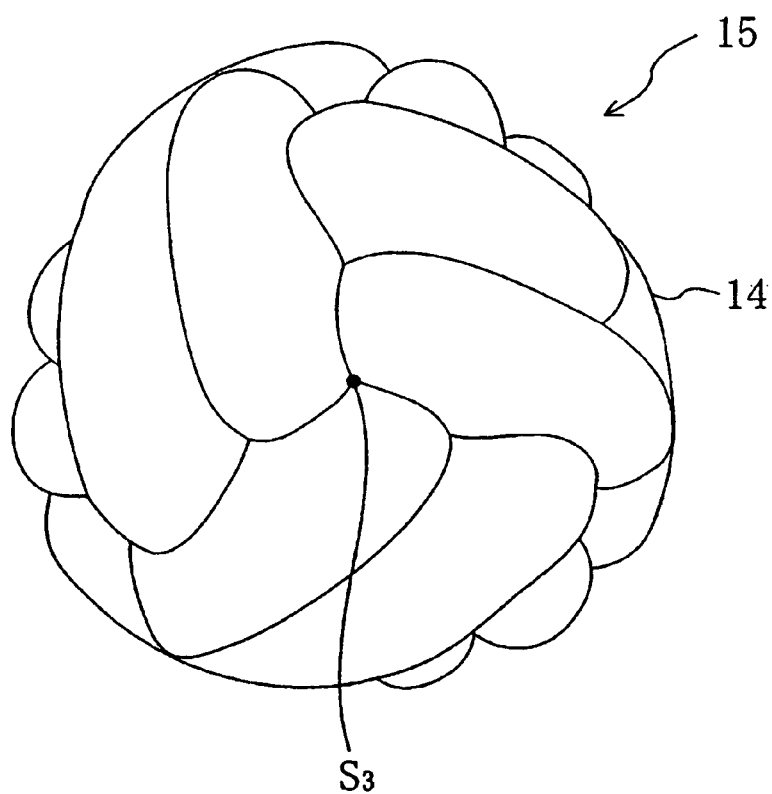
FIG. 6 is a drawing illustrating the structure of the apoferritin fine particles used in the embodiment 1.
Figure 7:
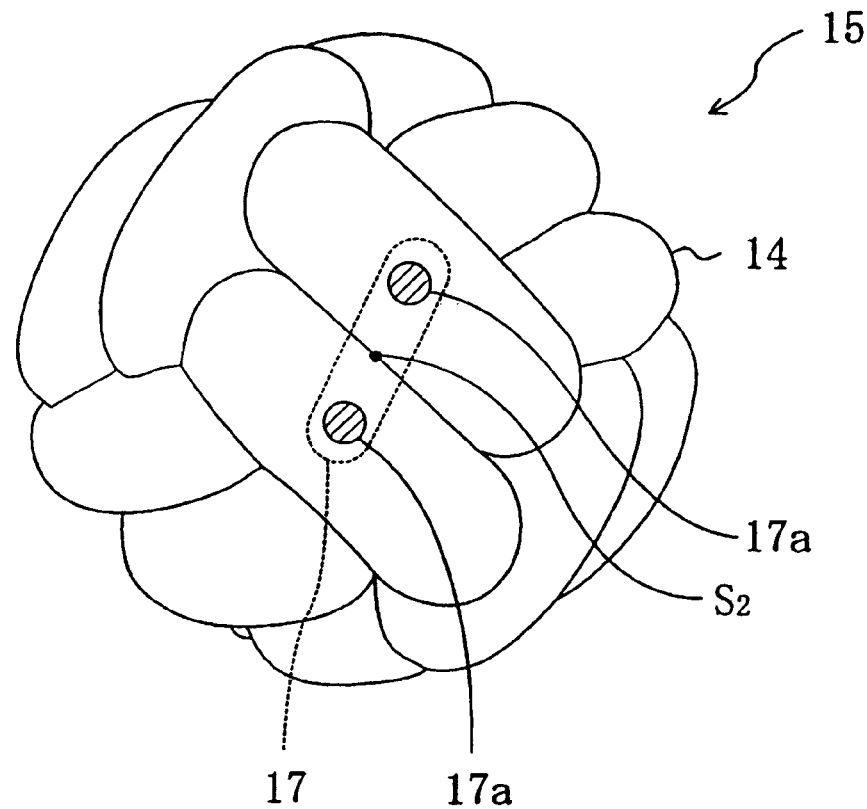
FIG. 7 is a drawing illustrating the structure of the apoferritin fine particles used in the embodiment 1.

The apoferritin fine particle 15 has an extremely highly symmetrical structure as described in the explanation for the above process. FIGS. 5 to 7 respectively present the figures viewed from the directions of different symmetric axes carried by the apoferritin fine particle 15. As shown in FIGS. 5 to 7, the apoferritin fine particle 15 has a four times symmetric axis S4, a three times symmetric axis S3 and a twice symmetric axis S2.

Because the apoferritin fine particle 15 has predominantly negative charge in its entirety, apoferritin fine particles 15 repel with each other under a neutral condition. Thus, the apoferritin fine particles 15 do not form an aggregate and thus diffuse within the liquid 16.

However, the apoferritin fine particle 15 has a site where a glutamic acid residue appears on the surface in the vicinity of the twice symmetric axis S2 (glutamic acid appearing site) 17, as shown in FIG. 7. Therefore, two apoferritin fine particles 15 can form a binding via an electrostatic interaction (salt bridge) so that they face one another with an ion (for example, cadmium ion or the like) sandwiched between the respective glutamic acid appearing sites 17. The binding via an electrostatic interaction as described above is herein referred to as a "salt bridge".

Figure 8:
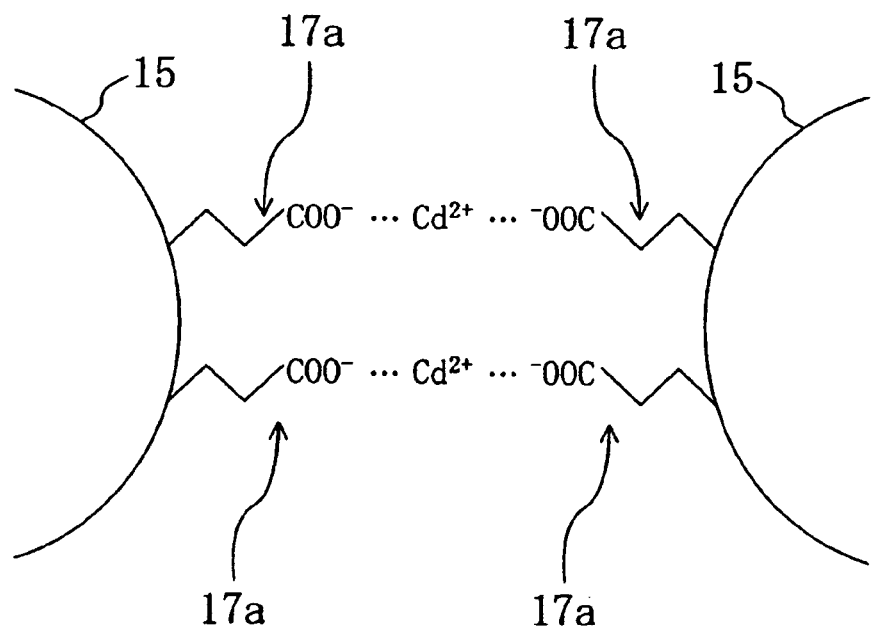
FIG. 8 is a drawing schematically illustrating the salt bridge formed between two apoferritin fine particles.

FIG. 8 is a drawing schematically illustrating the salt bridge formed between two apoferritin fine particles 15. As shown in FIG. 7, the glutamic acid appearing site 17 has a pair of glutamic acid residues 17a located on the surface of the site R2 in the vicinity of the twice symmetric axis S2. The glutamic acid residue 17a is present in each subunit 14 one by one. Upon forming the salt bridge, as shown in FIG. 8, a divalent cation (indicated as cadmium in the Figure) is sandwiched between each one of a pair of glutamic acid residues 17a and each one of the opposing pair of glutamic acid residues 17a. Therefore, when a salt bridge is formed between two apoferritin fine particles 15, free rotation of the two apoferritin fine particles are respectively inhibited. In addition, as shown in FIG. 3(a), mutual positional relationship of two apoferritin fine particles 15 is fixed directing to the same direction.

For the purpose of forming the salt bridge, it is necessary to have a cation (for example, cadmium ion and the like) which is divalent or more multivalent added in the liquid 16. The cation is preferably added in the range of 5 to 10 mM. In general, divalent cation is used.

Next, genetically engineered modification subjected to the apoferritin fine particle 15 is explained. The base sequence of the DNA coding for the apoferritin fine particle 15 is set out in SEQ ID NO: 1, whilst the amino acid sequence of the apoferritin fine particle 15 is set out in SEQ ID NO: 2. Because the apoferritin fine particle 15 is constituted from the identical 24 subunits 14, "base sequence of the DNA coding for the apoferritin fine particle 15" and "amino acid sequence of the apoferritin fine particle 15" herein mean the base sequence of the DNA coding for the subunit 14 and the amino acid sequence of the subunit 14, respectively.

The amino acid sequence of native apoferritin fine particle derived from bovine liver and the base sequence of the DNA encoding the same are known, and its tertiary structure has been also elucidated. In particular, native apoferritin fine particle has a channel connecting to the inside hollow core along the three times symmetric axis S3. There exist amino acids having negative charge under a neutral condition (acidic amino acid) around the channel.

The subunit of the native apoferritin fine particle is constituted from 175 amino acid residues. Among the amino acid residues, many of the acidic amino acid residues are located at the site R3 in the vicinity of the three times symmetric axis S3. The first to eighth amino acid residues of the native apoferritin fine particle are deleted upon processing in vivo. Therefore, the base at position 25 in the base sequence of the DNA of the apoferritin fine particle 15 of this embodiment (SEQ ID NO: 1) is denoted as a base at the first position, whilst tyrosine at position 9 is denoted as an amino acid at the first position in the amino acid sequence thereof (SEQ ID NO: 2).

The apoferritin fine particle 15 used in this embodiment is produced by using any known genetic recombination technique and protein expression method on the basis of the base sequence of the DNA set out in SEQ ID NO: 1. The apoferritin fine particle 15 includes amino acid substitution at amino acids located in the site R3 in the vicinity of the three times symmetric axis S3 with an amino acid having positive charge under a neutral condition (basic amino acid). Specifically, as set out in SEQ ID NO: 1 and 2, lysine at positions 112 and 113 in the amino acid sequence of the apoferritin fine particle 15 is respectively substituted from alanine and glutamine. Thus, the surface of the site R3 in the vicinity of the three times symmetric axis S3 has strongly positive charge. Accordingly, the apoferritin fine particle 15 binds to the surface of the substrate 11 which is negatively charged at the site R3 in the vicinity of the three times symmetric axis S3 via an electrostatic interaction.

Although the amino acids at positions 112 and 113 herein are substituted with lysine, other basic amino acids are also permitted as long as they are basic (i.e., arginine and histidine). However, in light of the electrostatic interaction with the substrate which is negatively charged, substitution with lysine at any of the positions is desired among these basic amino acids. In addition, the amino acid at position 112 and the amino acid at position 113 may be the same or different. Moreover, although substitution of the amino acids at positions 112 and 113 with a basic amino acid such as lysine was conducted in conjunction with the use of negatively charged substrate, to substitute the amino acids at positions 112 and 113 with an acidic amino acid (i.e., glutamic acid, aspartic acid, glutamine, asparagine, particularly glutamic acid, aspartic acid among these) having the counter polarity is allowed accompanied by using a positively charged substrate. Also in this instance, the amino acid at position 112 and the amino acid at position 113 may be the same or different. This aspect is similarly applied to the following embodiment 2 and below.

Meanwhile, positive charge and negative charge are present admixed on the surface of other sites than the site R3 in the vicinity of the three times symmetric axis S3 of the apoferritin fine particle 15, with negative charge being predominant in its entirety. Thus, in the step illustrated in the above FIG. 1(b), repulsive force acts between the surface of other sites than the site R3 in the vicinity of the three times symmetric axis S3 of the apoferritin fine particle 15 and the surface of the negatively charged substrate 11. Therefore, the three times symmetric axis S3 of the apoferritin fine particle 15 is fixed almost perpendicularly to the surface of the substrate 11.

In the step illustrated in FIG. 1(b), the pH of the liquid 16 is preferably adjusted to be in the range of 3 or greater and 11 or less so that the surface of the substrate 11 has negative charge and that the site R3 of the apoferritin fine particle 15 also has negative charge in the liquid 16. It is particularly preferred that the pH of the liquid 16 is adjusted to be in the range of 5 or greater and 10 or less.

Furthermore, in the step illustrated in the above FIG. 1(b), it is preferred that a liquid 16 including sufficiently diluted apoferritin fine particle 15 is prepared so that many cores are not generated which can originate the formation of a two-dimensional crystal film. Practically, it is preferred that the concentration of the apoferritin fine particle 15 in the liquid 16 is 100 µg/ml or less, and more preferably 30 µg/ml or less.

Alternatively, instead of using the liquid 16, a method in which a dispersion medium containing no apoferritin fine particle 15 is provided, and thereto immersed the substrate 11, followed by adding a colloidal solution containing the apoferritin fine particles 15 at a high concentration to this dispersion medium in an extremely gentle manner (for example, giving the final concentration of the apoferritin fine particle of 100 µg/ml over 10 hours) may be also employed.

Although the two-dimensional crystal film was formed on the surface of the substrate 11 in this embodiment, but not limited thereto. For example, it is possible to form the two-dimensional crystal film also on the surface of a liquid, liquid crystal or the like.

Furthermore, the surface of the substrate 11 is treated so that the apoferritin fine particles 15 are bound via an electrostatic interaction according to this embodiment. However, it may be constituted to utilize any other interaction (for example, hydrophilic interaction, hydrophobic interaction and complementarity of the dimensional standard), which is not limited to the electrostatic interaction.

Moreover, in the instance of using other protein fine particle instead of the apoferritin fine particle 15, the combination of the amino acid at the site to be bound to the surface of the substrate 11 and the charge of the surface of the substrate 11 is preferably selected to provide a combination of a basic amino acid and negative charge, or of an acidic amino acid and positive charge. These combinations result in facilitated binding between the protein fine particle and the surface of the substrate 11 via an electrostatic interaction under the pH condition described above.

When an amino acid which has repulsing charge to the surface charge of the substrate 11 is included at the site where the protein fine particles used are bound to the substrate 11, it is preferred that protein fine particles including genetically engineered substitution of a basic amino acid with an acidic amino acid are used instead so that binding is achieved via an electrostatic interaction.

In accordance with this embodiment, the substrate 11 with a SAM film formed on its surface is used. The SAM film is a single molecular film formed on the surface of the substrate 11, and can control the distance to the apoferritin fine particles 15 in a highly accurate manner. The surface of the substrate 11 may be covered with a single molecular film other than the SAM film. Further, a lipid bilayer film (LB film) comprising a phospholipid may be formed on the substrate 11.

Embodiment 2

In this embodiment, a process for producing a two-dimensional crystal film with fine particles being arranged at a high density in a highly accurate and regular manner on the surface of the substrate by bringing the site in the vicinity of the four times symmetric axis S4 of the apoferritin fine particle 15 bound to the surface of the substrate 11 is explained. This embodiment has the almost same constitution as that of the embodiment 1 as described above, and the summary of the process for producing the two-dimensional crystal film according to this embodiment is as illustrated in FIG. 1. However, the amino acid sequence of the apoferritin fine particle 15 is different.

The apoferritin fine particle 15 of this embodiment can form two pairs of salt bridges via a divalent cation with another apoferritin fine particle at each site R2 in the vicinity of the twice symmetric axis S2. Moreover, the apoferritin fine particle 15 used in this embodiment is subjected to genetically engineered modification so that each site R4 in the vicinity of the four times symmetric axis S4 has positive charge under a neutral condition.

Specifically, the apoferritin fine particle 15 of this embodiment is produced by using any known genetic recombination technique and protein expression method on the basis of the base sequence of the DNA set out in SEQ ID NO: 3. The apoferritin fine particle 15 includes the amino acid substitution at amino acids located in the site R4 in the vicinity of the four times symmetric axis S4 with an amino acid having positive charge under a neutral condition (basic amino acid). In particular, as set out in SEQ ID NO: 3 and 4, lysine at positions 149 and 151 in the amino acid sequence of the apoferritin fine particle 15 is respectively substituted from alanine and glutamine. Thus, the surface of the site R4 in the vicinity of the four times symmetric axis S4 has strongly positive charge. Accordingly, the apoferritin fine particle 15 binds to the surface of the substrate 11 which is negatively charged at the site R4 in the vicinity of the four times symmetric axis S4.

Meanwhile, positive charge and negative charge are present admixed on the surface of other sites than the site R4 in the vicinity of the four times symmetric axis S4 of the apoferritin fine particle 15, with negative charge being predominant in its entirety. Thus, repulsive force acts between the surface of other sites than the site R4 in the vicinity of the four times symmetric axis S4 of the apoferritin fine particle 15 and the surface of the negatively charged substrate 11. Therefore, the four times symmetric axis S4 of the apoferritin fine particle 15 is fixed almost perpendicularly to the surface of the substrate 11.

Figure 9:
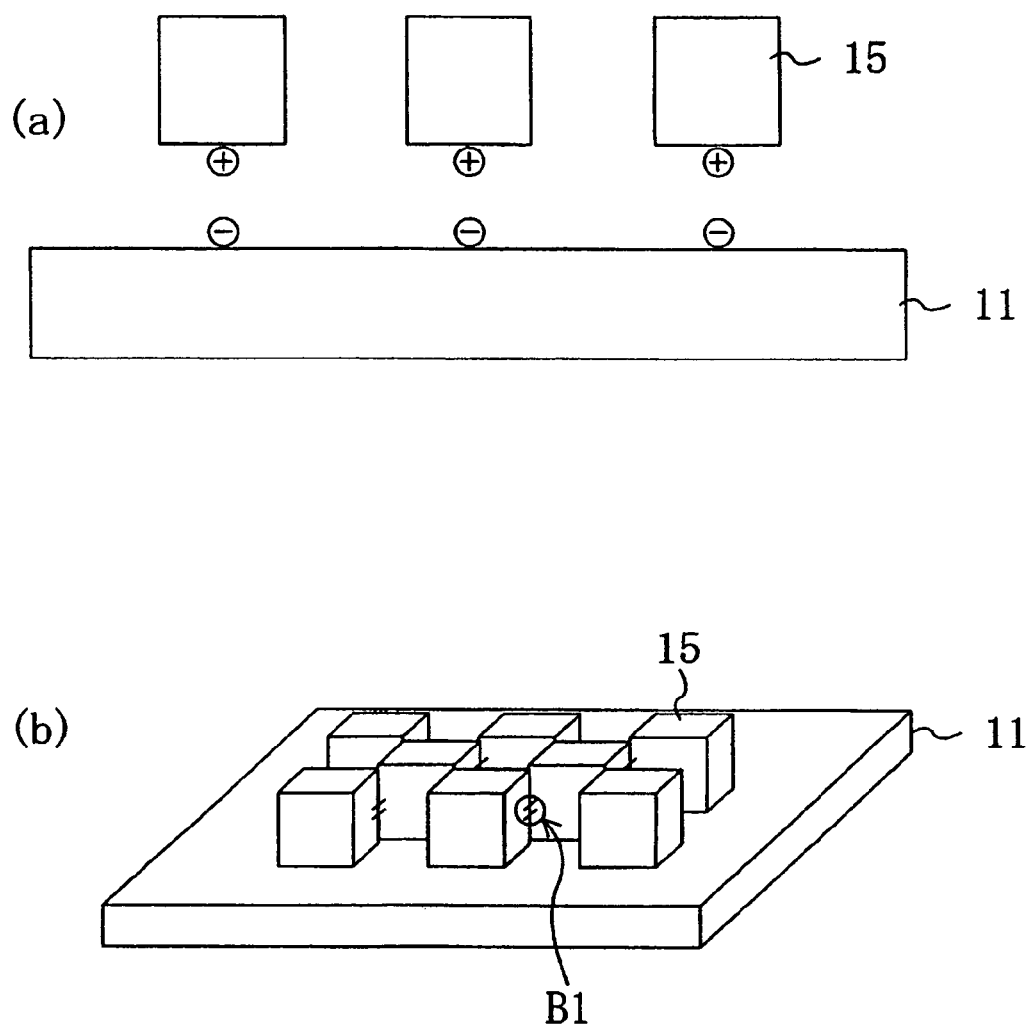
FIG. 9 is a drawing for explaining the step shown in FIG. 1(b) in more detail: (a) is a cross-sectional drawing; and (b) is a top view of the same.

FIG. 9(a) and FIG. 9(b) are a cross-sectional drawing and a top view for explaining the step shown in FIG. 1(b) in more detail. In the step illustrated in FIG. 1 (b), binding via an electrostatic interaction is executed with the substrate 11 at either one of the sites R4 in the vicinity of the four times symmetric axes S4 through using the liquid 16 prepared as described above and the substrate 11. Upon the binding, the apoferritin fine particles 15 are sparsely present on the surface of the substrate 11 in a state where the four times symmetric axis S4 directs almost perpendicular to the surface of the substrate 11 as illustrated in FIG. 9(a). In addition, when the binding of the apoferritin fine particles 15 proceeds, adjacent apoferritin fine particles 15 form salt bridges B1 with each other at the site R2, as shown in FIG. 9(b). Therefore, the particles bind to the surface of the substrate 11 while forming salt bridges B1 with each other at the sites R2 in a state where the four times symmetric axis S4 directs almost perpendicular to the surface of the substrate 11. This event occurs successively on the surface of the substrate 11, and thus results in the formation of a two-dimensional crystal film which is four times symmetry, as shown in FIG. 9(b).

Figure 10:
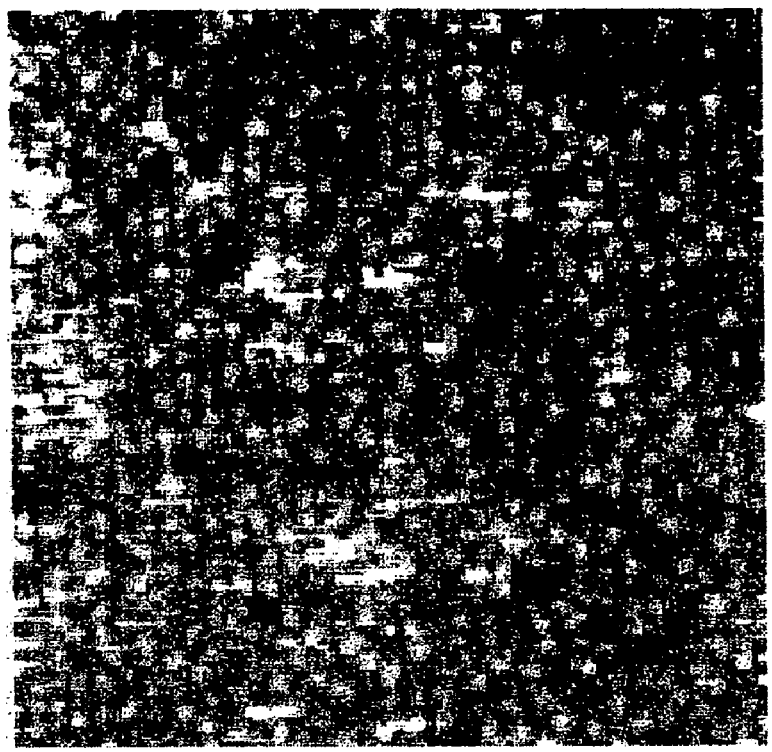
FIG. 10 is an electron microscopic photograph of the two-dimensional crystal film obtained according to embodiment 2.

FIG. 10 is an electron microscopic photograph of the two-dimensional crystal film obtained according to this embodiment. The two-dimensional crystal film schematically illustrated in FIG. 9(b) is a film including apoferritin fine particles 15 arranged in a checkered pattern. However, actual apoferritin fine particle 15 is almost spherical. Therefore, spaces among each of the apoferritin fine particles 15 are diminished as shown in FIG. 10.

Although processes for producing two-dimensional crystal films which are three times symmetric and four times symmetric hereinabove, the present invention is not limited thereto. When the site R2 in the vicinity of the twice symmetric axis S2 is bound to the surface of the substrate 11, and apoferritin fine particles having three or more mutual binding sites are provided, it is also possible to produce a twice symmetric two-dimensional crystal film by the process illustrated in FIG. 1. Therefore, when a protein such as apoferritin having plural number of symmetric axes is used, directions of the protein to the substrate can be changed. More specifically, when the direction of the protein to the substrate is intended to direct as illustrated in FIG. 3(b), substitution with a basic amino acid at the sites R3 shown in FIG. 2 may be conducted. When the direction of the protein to the substrate is intended to direct as illustrated in FIG. 9(b), substitution with a basic amino acid at the sites R4 shown in FIG. 2 may be conducted. With regard to the twice symmetric axis not shown in the Figure, substitution with a basic amino acid at the sites R2 shown in FIG. 2 may be conducted. The directions of a protein to the substrate can be changed even though the same protein is used, when a negatively charged substrate (positively charged substrate in the instances where sites R2 to R4 are acidic amino acids) is thereafter brought into contact. It is also enabled to alter the function of a fine particle film accordingly.

Embodiment 3

According to this embodiment, a method of utilizing the two-dimensional crystal film produced in the embodiments 1 and 2 as described above is explained.

Figure 11:
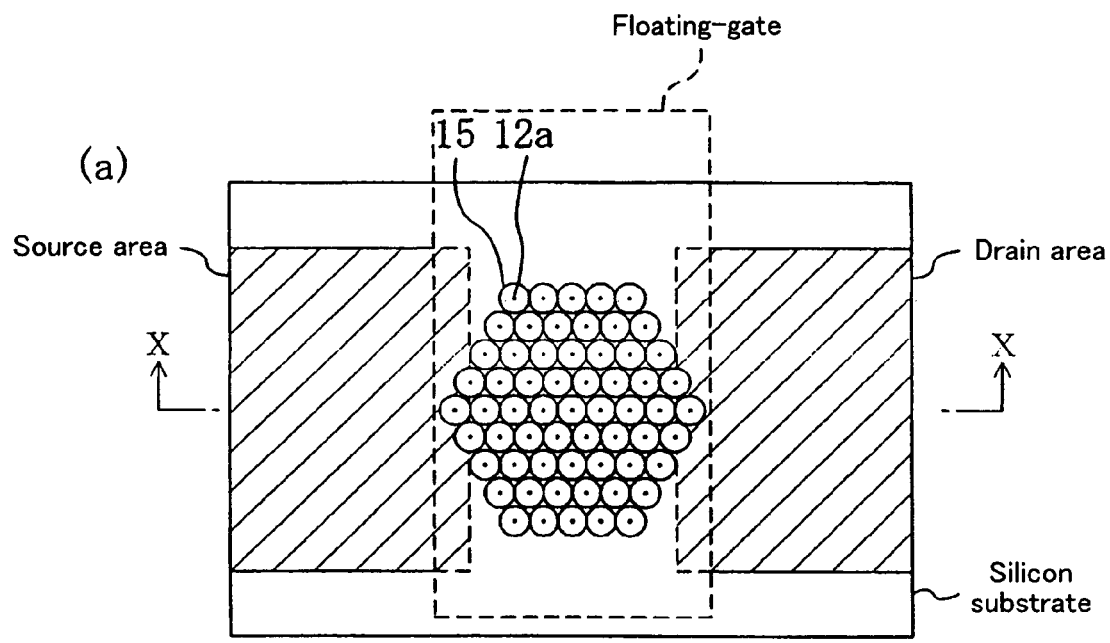
FIG. 11 is a drawing illustrating EP-ROM: (a) is a top view; and (b) is a cross-sectional view of the same.
Figure 11:
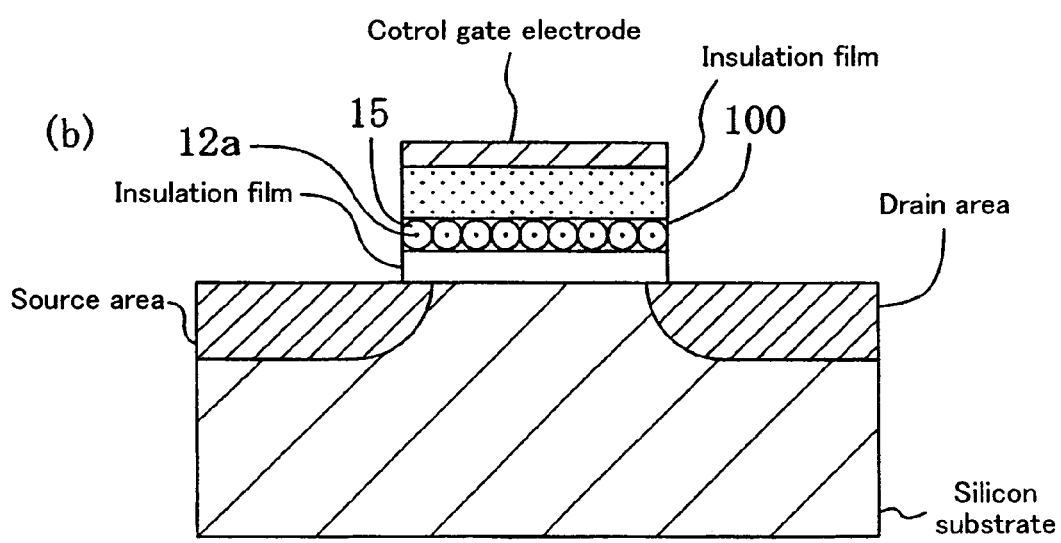
Figure 12:
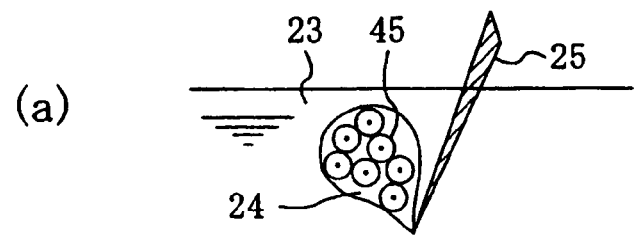
FIG. 12 is a drawing illustrating a process for producing a conventional fine particle film. In the Figure, (a) illustrates a step for injecting a liquid 24 with protein fine particles 45 dispersed therein into a sucrose solution 23; (b) illustrates a step in which the liquid 24 is elevated; (c) illustrates a step in which the protein fine particles 45 attach beneath the amorphous film 26; (d) illustrates a step in which the film 28 is transferred to the surface of the substrate 21.
Figure 12:
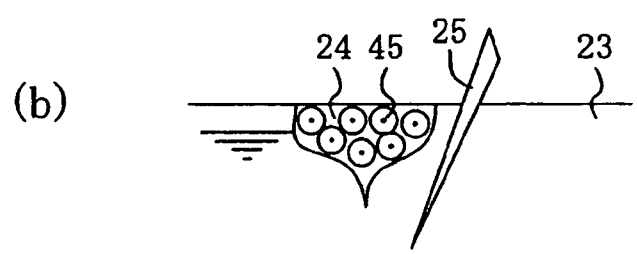
Figure 12:
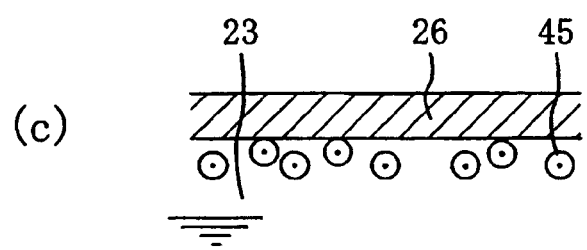
Figure 12:
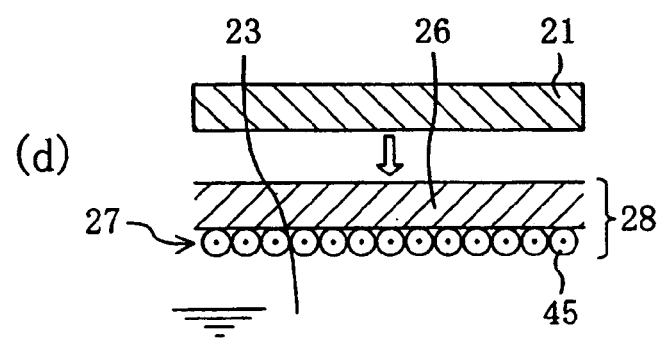

First, examples of the utilization of the two-dimensional crystal film produced in the embodiments 1 and 2 as described above include floating-gates such as EP-ROM, E2P-ROM and the like. FIGS. 11(a) and (b) are a top view and a cross-sectional view of EP-ROM in which the two-dimensional crystal film produced according to the process demonstrated in the embodiment 1 described above is used as a floating-gate.

In the two-dimensional crystal film produced in the embodiment 1 as described above, metal particles 12a which are included in the apoferritin fine particles 15 are arranged at high density in a highly accurate and regular manner with an insulated state each other. Thus, to precisely control number of the metal particles arranged on an insulation film is enabled by patterning and the like of a two-dimensional crystal film 100. The electrical charge accumulated on the floating-gate can be preciously controlled by precisely controlling the number of metal particles. Therefore, scattering of the variation amount Vth of threshold voltage for each memory cell before and after the writing can be suppressed. When scattering of the variation amount Vth of threshold voltage for each memory cell before and after the writing is suppressed, the variation amount Vth of threshold voltage can be set to be smaller than ever before. In other words, EP-ROM and E2P-ROM can be obtained which are capable of operating at lower voltage than ever before.

Although the two-dimensional crystal film 100 may be patterned as described above in order to preciously control the number of the metal particles arranged on the insulation film, other methods may be also employed. In particular, a silicon substrate covered with an insulation film may be used as the substrate 11 in the embodiment 1 as described above, and among the surface of the insulation film, an area to be positively charged may be a regular hexagon. Thus, the apoferritin fine particles 15 are thereby arranged at a high density in a highly accurate and regular manner along the regular hexagon. Therefore, the number of the metal particles 12a included in the apoferritin fine particles 15 can be preciously controlled depending on the size of area of the regular hexagon.

Further, the two-dimensional crystal films produced in the embodiments 1 and 2 as described above can be also utilized for producing a magnetic disc.

In particular, a two-dimensional crystal film is produced using apoferritin fine particles 15 including a magnetic material particle therein, in the embodiments 1 and 2 as described above. Next, the apoferritin fine particles 15 are removed from thus resulting two-dimensional crystal film by e.g., heat treatment or the like to leave the inside magnetic material alone. Accordingly, a magnetic disc with high memory density is obtained which includes magnetic material particles arranged at a high density in a highly accurate and regular manner on the surface of the recording surface.

Furthermore, the two-dimensional crystal film produced in the embodiments 1 and 2 as described above can be also utilized in producing a biosensor such as a nucleotide sensor.

In particular, a two-dimensional crystal film is produced using apoferritin fine particles 15 including a gold particle in the embodiments 1 and 2 as described above. Next, the apoferritin fine particles 15 are removed from thus resulting two-dimensional crystal film to leave the inside gold particles alone. By binding a thiol DNA to these gold particles, a nucleotide sensor with extremely high SN ratio can be obtained having the thiol DNA arranged at a high density in a highly accurate manner.

According to the present invention, a two-dimensional crystal film with fine particles having a diameter of nanometer size which are arranged at a high density in a highly accurate and regular manner is obtained.

INDUSTRIAL APPLICAPILITY

As described hereinabove, the two-dimensional crystal film comprising protein fine particles according to the present invention is useful in crystal structure analyses of a protein by an electron microscope. Furthermore, the two-dimensional crystal film according to the present invention is also useful in producing floating-gates such as EP-ROM and E2P-ROM, and magnetic discs.

[FREE TEXT OF SEQUENCE LISTING]

<223> of SEQ ID NO: 1: recombinant DNA of liver apoferritin of *Equus cebellus*

<223> of SEQ ID NO: 2: recombinant liver apoferritin of *Equus cebellus*

<223> of SEQ ID NO: 3: recombinant DNA of liver apoferritin of *Equus cebellus*

<223> of SEQ ID NO: 4: recombinant liver apoferritin of *Equus cebellus*

---

What is claimed is:

1. A fine particle film comprising a substrate and plural number of protein fine particles which are arranged on the surface of said substrate in a plane direction parallel to the surface of said substrate,
   wherein each of said protein fine particles is a modified apoferritin SEQ ID NO. 2 in which glycine at position 149 and glutamine at position 151 are substituted with a basic amino acid;
   said substrate is negatively charged;
   each of adjacent two protein particles has a —COO⁻ group; and
   a divalent cation is sandwiched between the —COO⁻ groups carried by said adjacent two protein particles, respectively.

2. The fine particle film according to claim 1, wherein glycine at position 149 in SEQ ID NO. 2 is substituted with lysine.

3. The fine particle film according to claim 1, wherein glutamine at position 151 in SEQ ID NO. 2 is substituted with lysine.

4. The fine particle film according to claim 1, wherein glycine at position 149 in SEQ ID NO. 2 is substituted with lysine and glutamine at position 151 in SEQ ID NO. 3 is substituted with lysine.

5. The fine particle film according to claim 1, wherein said divalent cation is $Cd^{2+}$.

* * * * *

UNITED STATES PATENT AND TRADEMARK OFFICE
CERTIFICATE OF CORRECTION

PATENT NO.        : 7,037,728 B2                                              Page 1 of 1
APPLICATION NO.   : 10/617955
DATED             : May 2, 2006
INVENTOR(S)       : Ichiro Yamashita It is certified that error appears in the above-identified patent and that said Letters Patent is hereby corrected as shown below:

IN THE CLAIMS:
Column 17, line 39, between "apoferritin" and "SEQ ID No. 2", insert -- of --.

Signed and Sealed this

Seventeenth Day of October, 2006

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 504
<212> TYPE: DNA
<213> ORGANISM: Artificial Sequence
<220> FEATURE:
<223> OTHER INFORMATION: Recombinant DNA of Liver Apoferritin of Equus
                        cebellus

<400> SEQUENCE: 1
tattctactg aagtggaggc cgccgtcaac cgcctggtca acctgtacct gcgggcctcc       60
tacacctacc tctctctggg cttctatttc gaccgcgacg atgtggctct ggagggcgta      120
tgccacttct tccgcgagtt ggcggaggag aagcgcgagg gtgccgagcg tctcttgaag      180
atgcaaaacc agcgcggcgg ccgcgctctc ttccaggact tgcagaagcc gtcccaggat      240
gaatggggta caacccagc cgccatgaaa gccgccattg tcctggagaa gagcctgaac      300
caggcccttt tggatctgca tgccctgggt tctaggaggg cagaccccca tctctgtgac      360
ttcttggaga gccacttcct agacgaggag gtgaaactca tcaagaagat gggcgaccat      420
ctgaccaaca tccagaggct cgttggctcc caagctgggc tgggcgagta tctctttgaa      480
aggctcactc tcaagcacga ctaa                                              504

<210> SEQ ID NO 2
```

```
<211> LENGTH: 167
<212> TYPE: PRT
<213> ORGANISM: Artificial Sequence
<220> FEATURE:
<223> OTHER INFORMATION: Recombinant Liver Apoferritin of Equus cebellus

<400> SEQUENCE: 2
```

Tyr Ser Thr Glu Val Glu Ala Ala Val Asn Arg Leu Val Asn Leu Tyr
1               5                   10                  15

Leu Arg Ala Ser Tyr Thr Tyr Leu Ser Leu Gly Phe Tyr Phe Asp Arg
            20                  25                  30

Asp Asp Val Ala Leu Glu Gly Val Cys His Phe Phe Arg Glu Leu Ala
            35                  40                  45

Glu Glu Lys Arg Glu Gly Ala Glu Arg Leu Leu Lys Met Gln Asn Gln
        50                  55                  60

Arg Gly Gly Arg Ala Leu Phe Gln Asp Leu Gln Lys Pro Ser Gln Asp
65                  70                  75                  80

Glu Trp Gly Thr Thr Pro Asp Ala Met Lys Ala Ala Ile Val Leu Glu
                85                  90                  95

Lys Ser Leu Asn Gln Ala Leu Leu Asp Leu His Ala Leu Gly Ser Lys
            100                 105                 110

Lys Ala Asp Pro His Leu Cys Asp Phe Leu Glu Ser His Phe Leu Asp
            115                 120                 125

Glu Glu Val Lys Leu Ile Lys Lys Met Gly Asp His Leu Thr Asn Ile
        130                 135                 140

Gln Arg Leu Val Gly Ser Gln Ala Gly Leu Gly Glu Tyr Leu Phe Glu
145                 150                 155                 160

Arg Leu Thr Leu Lys His Asp
                165

```
<210> SEQ ID NO 3
<211> LENGTH: 504
<212> TYPE: DNA
<213> ORGANISM: Artificial Sequence
<220> FEATURE:
<223> OTHER INFORMATION: Recombinant DNA of Liver Apoferritin of Equus
                        cebellus

<400> SEQUENCE: 3
tattctactg aagtggaggc cgccgtcaac cgcctggtca acctgtacct gcgggcctcc        60
tacacctacc tctctctggg cttctatttc gaccgcgacg atgtggctct ggagggcgta       120
tgccacttct tccgcgagtt ggcggaggag aagcgcgagg gtgccgagcg tctcttgaag       180
atgcaaaacc agcgcggcgg ccgcgctctc ttccaggact tgcagaagcc gtcccaggat       240
gaatggggta caaccccaga cgccatgaaa gccgccattg tcctggagaa gagcctgaac       300
caggcccttt tggatctgca tgccctgggt tctaggaggg cagaccccca tctctgtgac       360
ttcttggaga gccacttcct agacgaggag gtgaaactca tcaagaagat gggcgaccat       420
ctgaccaaca tccagaggct cgttggctcc aagctgggc tgggcgagta tctctttgaa        480
aggctcactc tcaagcacga ctaa                                              504

<210> SEQ ID NO 4
<211> LENGTH: 167
<212> TYPE: PRT
<213> ORGANISM: Artificial Sequence
<220> FEATURE:
<223> OTHER INFORMATION: Recombinant Liver of Apoferritin of Equus
                        cebellus
```

-continued

```
<400> SEQUENCE: 4

Tyr Ser Thr Glu Val Glu Ala Ala Val Asn Arg Leu Val Asn Leu Tyr
1               5                   10                  15

Leu Arg Ala Ser Tyr Thr Tyr Leu Ser Leu Gly Phe Tyr Phe Asp Arg
                20                  25                  30

Asp Asp Val Ala Leu Glu Gly Val Cys His Phe Phe Arg Glu Leu Ala
            35                  40                  45

Glu Glu Lys Arg Glu Gly Ala Glu Arg Leu Leu Lys Met Gln Asn Gln
        50                  55                  60

Arg Gly Gly Arg Ala Leu Phe Gln Asp Leu Gln Lys Pro Ser Gln Asp
65                      70                  75                  80

Glu Trp Gly Thr Thr Pro Asp Ala Met Lys Ala Ala Ile Val Leu Glu
                85                  90                  95

Lys Ser Leu Asn Gln Ala Leu Leu Asp Leu His Ala Leu Gly Ser Ala
                100                 105                 110

Gln Ala Asp Pro His Leu Cys Asp Phe Leu Glu Ser His Phe Leu Asp
            115                 120                 125

Glu Glu Val Lys Leu Ile Lys Lys Met Gly Asp His Leu Thr Asn Ile
        130                 135                 140

Gln Arg Leu Val Lys Ser Lys Ala Gly Leu Gly Glu Tyr Leu Phe Glu
145                 150                 155                 160

Arg Leu Thr Leu Lys His Asp
                165
```